(12) United States Patent
Werth

(10) Patent No.: US 9,605,782 B2
(45) Date of Patent: Mar. 28, 2017

(54) SANITARY RETAINER

(75) Inventor: Albert A. Werth, Ft. Myers, FL (US)

(73) Assignee: SAINT-GOBAIN PERFORMANCE PLASTICS CORPORATION, Solon, OH (US)

( * ) Notice: Subject to any disclaimer, the term of this patent is extended or adjusted under 35 U.S.C. 154(b) by 1075 days.

(21) Appl. No.: 12/752,803

(22) Filed: Apr. 1, 2010

(65) Prior Publication Data

US 2010/0253075 A1     Oct. 7, 2010

Related U.S. Application Data

(60) Provisional application No. 61/166,028, filed on Apr. 2, 2009.

(51) Int. Cl.
| F16L 21/06 | (2006.01) |
| F16L 23/04 | (2006.01) |
| F16L 37/138 | (2006.01) |
| A61M 39/10 | (2006.01) |

(52) U.S. Cl.
CPC ............. *F16L 23/04* (2013.01); *F16L 37/138* (2013.01); *A61M 2039/1038* (2013.01); *A61M 2039/1066* (2013.01); *Y10T 29/49945* (2015.01); *Y10T 29/53* (2015.01)

(58) Field of Classification Search
USPC .... 285/3, 243, 322, 384, 385, 324; 403/299, 403/307, 338
See application file for complete search history.

(56) References Cited

U.S. PATENT DOCUMENTS

| 36,410 | A |   | 9/1862 | Jucket |
| 850,731 | A |   | 4/1907 | Christensen et al. |
| 919,913 | A | * | 4/1909 | Miller ........................... 285/384 |
| 1,390,564 | A |   | 9/1921 | Knorr |
| 1,441,154 | A |   | 4/1922 | Johnson |
| 2,466,526 | A |   | 4/1949 | Wolfram |
| 2,832,598 | A | * | 4/1958 | Strub ................... A63D 15/086 285/323 |
| 2,868,564 | A |   | 1/1959 | Arras |

(Continued)

FOREIGN PATENT DOCUMENTS

| DE | 10259515 A1 | 7/2004 |
| EP | 0515930 A1 | 12/1992 |

(Continued)

OTHER PUBLICATIONS

EP Search Report (Dated: Oct. 21, 2009); Appl. No. 04795367.4; Applicant: Twin Bay Medical, Inc.

(Continued)

*Primary Examiner* — Aaron Dunwoody
(74) *Attorney, Agent, or Firm* — Chi S. Kim; Abel Law Group, LLP

(57) ABSTRACT

A retainer for connecting a pair of sanitary fittings each having a first end and a second end, the second ends each having a flanged portion, includes a first member having a through center aperture, the first member adapted to receive at least a portion of each of the flanged portions and a second member having a through center aperture and engageable over the first member, the second member adapted to provide a compressive force to sealingly connect the flanged portions when the first and second members are in an assembled configuration.

8 Claims, 5 Drawing Sheets

(56) References Cited

U.S. PATENT DOCUMENTS

| | | |
|---|---|---|
| 2,940,778 A | 6/1960 | Kaiser |
| 2,958,549 A | 11/1960 | Spafford |
| 3,325,194 A | 6/1967 | Grawey |
| 3,406,991 A | 10/1968 | Decker, Jr. et al. |
| 3,568,977 A * | 3/1971 | Nelson .................. 251/148 |
| 3,589,752 A | 6/1971 | Spencer et al. |
| 3,653,692 A | 4/1972 | Henson |
| 3,915,167 A | 10/1975 | Waterman |
| 4,049,301 A | 9/1977 | Schenk |
| 4,247,076 A | 1/1981 | Larkin |
| 4,250,348 A * | 2/1981 | Kitagawa .................. 174/655 |
| 4,303,263 A | 12/1981 | Legris |
| 4,328,979 A * | 5/1982 | Stoll .................. 285/148.14 |
| 4,412,693 A | 11/1983 | Campanini |
| 4,442,994 A | 4/1984 | Logsdon |
| 4,487,205 A | 12/1984 | Di Giovanni et al. |
| 4,487,336 A | 12/1984 | Sneider |
| 4,564,222 A | 1/1986 | Loker et al. |
| 4,588,160 A | 5/1986 | Flynn et al. |
| 4,630,630 A | 12/1986 | Reynolds et al. |
| 4,632,435 A | 12/1986 | Polyak |
| 4,640,530 A | 2/1987 | Abbes et al. |
| 4,723,948 A | 2/1988 | Clark et al. |
| 4,736,925 A | 4/1988 | Kamstrup-Larsen et al. |
| 4,796,856 A | 1/1989 | Munini |
| 4,880,414 A | 11/1989 | Whipple |
| 4,890,866 A | 1/1990 | Arp |
| 4,906,030 A | 3/1990 | Yokomatsu et al. |
| 4,944,485 A | 7/1990 | Daoud et al. |
| 5,060,987 A | 10/1991 | Miller |
| 5,074,600 A | 12/1991 | Weinhold |
| 5,076,614 A | 12/1991 | Yokomatsu et al. |
| 5,149,145 A | 9/1992 | Yokomatsu et al. |
| 5,150,924 A | 9/1992 | Yokomatsu et al. |
| 5,203,056 A | 4/1993 | Funk et al. |
| 5,238,218 A | 8/1993 | Mackal |
| 5,240,289 A | 8/1993 | Gottling et al. |
| 5,240,291 A | 8/1993 | Zornow |
| 5,271,649 A | 12/1993 | Gromotka |
| 5,275,447 A | 1/1994 | McNab |
| 5,318,546 A | 6/1994 | Bierman |
| 5,361,806 A | 11/1994 | Lalikos et al. |
| 5,476,291 A | 12/1995 | Reneau |
| 5,536,258 A | 7/1996 | Folden |
| 5,584,513 A | 12/1996 | Sweeney et al. |
| 5,590,859 A | 1/1997 | Lord |
| 5,601,191 A | 2/1997 | Meador |
| 5,622,393 A | 4/1997 | Elbich et al. |
| 5,658,266 A | 8/1997 | Colacello et al. |
| 5,709,413 A | 1/1998 | Salyers |
| 5,713,912 A | 2/1998 | Porter |
| 5,725,447 A | 3/1998 | Friedmann et al. |
| 5,729,872 A | 3/1998 | Ginocchio |
| 5,882,047 A | 3/1999 | Ostrander et al. |
| 5,909,902 A | 6/1999 | Seabra |
| 5,984,378 A | 11/1999 | Ostrander et al. |
| 6,010,162 A | 1/2000 | Grau et al. |
| 6,039,725 A | 3/2000 | Moenning et al. |
| 6,101,684 A | 8/2000 | Ginocchio |
| 6,113,062 A | 9/2000 | Schnell et al. |
| 6,155,607 A * | 12/2000 | Hewitt et al. .................. 285/81 |
| 6,155,610 A | 12/2000 | Godeau et al. |
| 6,170,887 B1 | 1/2001 | Salomon-Bahls et al. |
| 6,173,926 B1 | 1/2001 | Elvegaard |
| 6,234,448 B1 | 5/2001 | Porat |
| 6,261,254 B1 | 7/2001 | Baron et al. |
| 6,390,721 B1 | 5/2002 | Wilson, II et al. |
| 6,422,529 B1 | 7/2002 | Adelberg |
| 6,435,568 B1 | 8/2002 | Fukano et al. |
| 6,488,318 B1 | 12/2002 | Shim |
| 6,644,618 B1 | 11/2003 | Balboa |
| 6,676,091 B2 | 1/2004 | Hauer |
| 6,679,529 B2 | 1/2004 | Johnson et al. |
| 6,708,377 B2 | 3/2004 | Maunder |
| 6,755,445 B2 | 6/2004 | Balamuta et al. |
| 6,796,586 B2 | 9/2004 | Werth |
| 6,860,521 B2 | 3/2005 | Berg |
| 6,908,120 B2 | 6/2005 | Tomita et al. |
| 7,090,257 B2 | 8/2006 | Werth |
| 7,284,137 B2 | 10/2007 | Clark et al. |
| 7,284,731 B1 | 10/2007 | Johnson et al. |
| 7,370,889 B2 | 5/2008 | Maunder et al. |
| 2002/0043804 A1 * | 4/2002 | Shen .................. F16L 19/075 285/322 |
| 2003/0047943 A1 | 3/2003 | Berg |
| 2003/0188401 A1 | 10/2003 | Huang |
| 2003/0193190 A1 | 10/2003 | Werth |
| 2004/0045447 A1 | 3/2004 | Navarro |
| 2004/0232697 A1 | 11/2004 | Tomita et al. |
| 2005/0082826 A1 | 4/2005 | Werth |
| 2005/0084327 A1 | 4/2005 | Chelchowski et al. |
| 2006/0131465 A1 | 6/2006 | Lynch, Jr. et al. |
| 2008/0169646 A1 | 7/2008 | Werth |
| 2008/0272590 A1 | 11/2008 | Howard et al. |
| 2008/0279039 A1 | 11/2008 | Furey |

FOREIGN PATENT DOCUMENTS

| | | |
|---|---|---|
| EP | 0762034 A1 | 3/1997 |
| FR | 1052094 | 1/1954 |
| JP | 06159573 A | 6/1994 |
| JP | H06241362 A | 8/1994 |
| JP | 2002525542 A | 8/2002 |
| JP | 2004347074 A1 | 12/2004 |
| KR | 1019910008238 B1 | 10/1991 |
| KR | 1019930009058 B1 | 9/1993 |
| KR | 200302163 Y1 | 1/2003 |
| KR | 200269757 Y1 | 4/2010 |
| WO | 9813637 A1 | 4/1998 |
| WO | 2005037343 A2 | 4/2005 |

OTHER PUBLICATIONS

Notification, Search Report and Written Opinion of the International Searching Authority dated Aug. 6, 2010 from the corresponding International Application No. PCT/US2010/020458 filed Jan. 8, 2010.

International Search Report and Written Opinion, dated Oct. 28, 2005, from the International Application No. PCT/US04/34190.

Written Opinion of the ISA and International Search Report dated Aug. 25, 2009 from the corresponding International Patent Application No. PCT/US2009/031257 filed Jan. 16, 2009.

Notification of Transmittal, the International Search Report and the Written Opinion of the International Searching Authority from the corresponding International Application No. PCT/US2010/029730 dated Jan. 5, 2011.

* cited by examiner

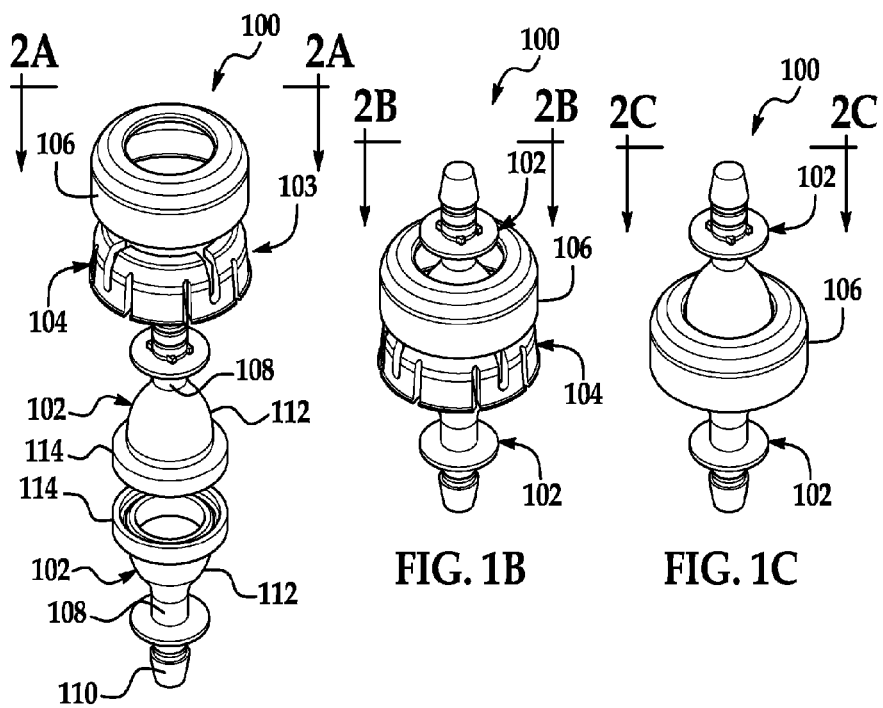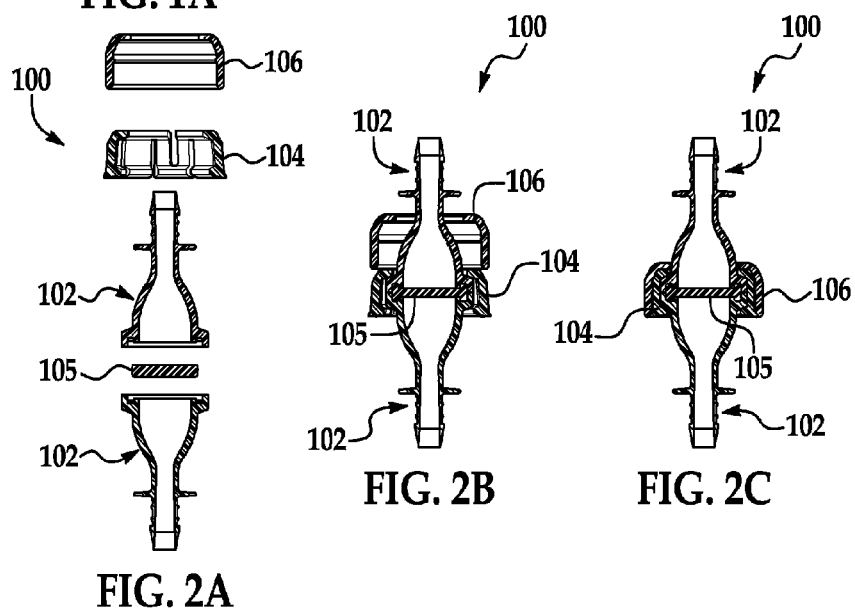

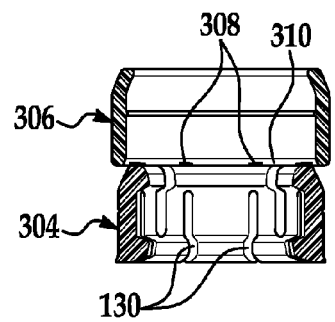
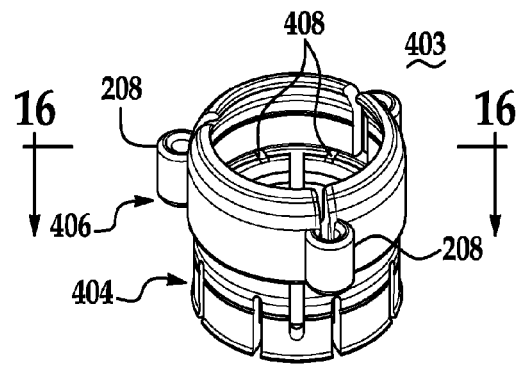
FIG. 13    FIG. 14
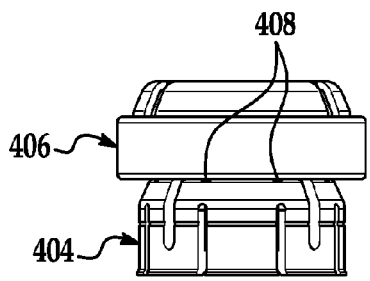
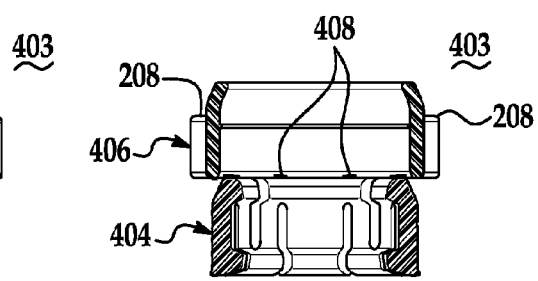
FIG. 15    FIG. 16
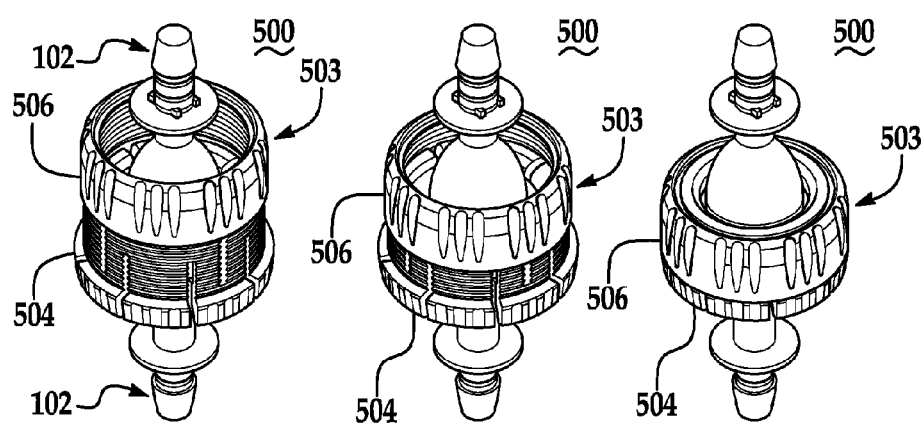
FIG. 17A    FIG. 17B    FIG. 17C

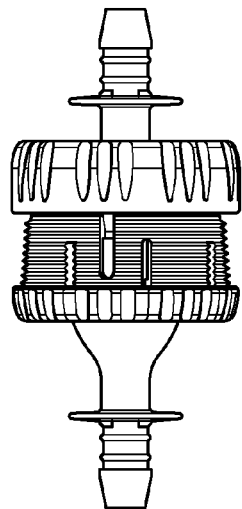
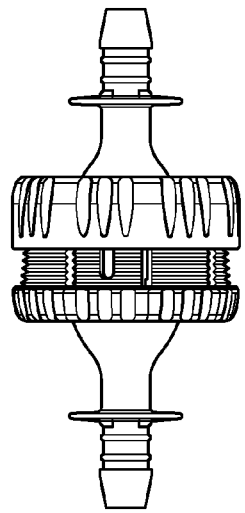
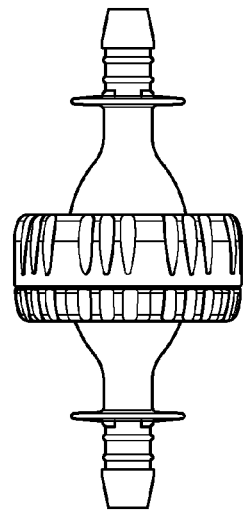
FIG. 18A    FIG. 18B    FIG. 18C
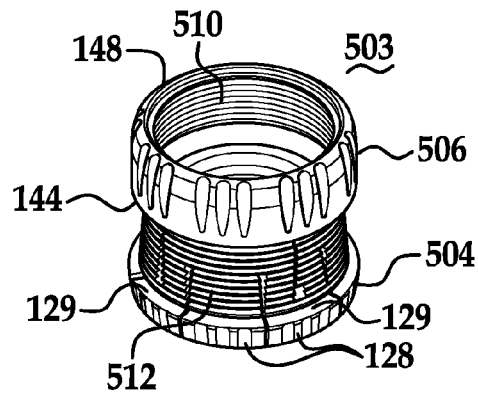
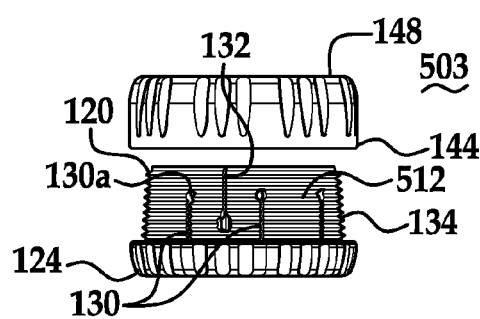
FIG. 19    FIG. 20
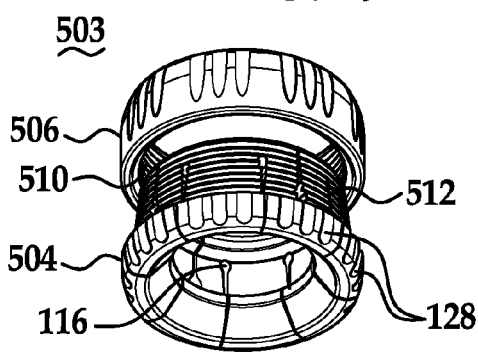
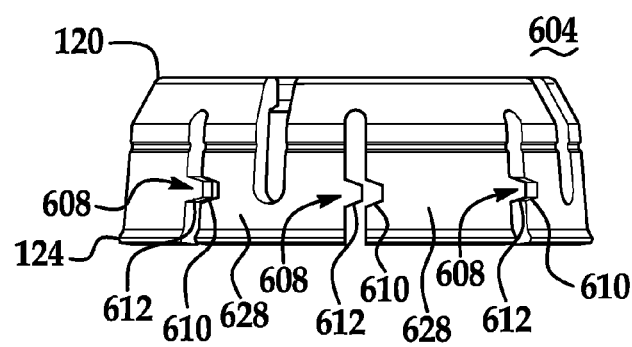
FIG. 21    FIG. 22

SANITARY RETAINER

CROSS-REFERENCE TO RELATED APPLICATIONS

This application claims priority to U.S. Provisional Application Ser. No. 61/166,028, filed Apr. 2, 2009, which is hereby incorporated by reference in its entirety.

FIELD OF THE INVENTION

The present invention generally pertains to a sanitary retainer connecting a pair of sanitary fittings.

BACKGROUND

Flexible tubing made of plastic or rubber is widely used in the medical, pharmaceutical, biopharmaceutical, food and beverage and other laboratory environments. For certain assemblies involving connections from a medical instrument to a patient, stainless steel connectors or clamps have been used to connect ends of the flexible tubing together. Stainless steel connectors or clamps have the advantage of being capable of sterilization and therefore being resusable. However, stainless steel connectors can be expensive to manufacture and may not completely protect against cross contamination.

SUMMARY

Embodiments of a retainer for connecting a pair of sanitary fittings are disclosed herein. The sanitary fittings each have a first end and a second end and the second ends each have a flanged portion. The retainer includes a first member having a through center aperture. The first member is adapted to receive at least a portion of each of the flanged portions. The retainer also includes a second member having a through center aperture and engageable over the first member. The second member is adapted to provide a compressive force to sealingly connect the flanged portions when the first and second members are in an assembled configuration.

Embodiments of a method for sealingly connecting a first sanitary fitting and a second sanitary fitting with a retainer are also disclosed herein. The retainer has first and second members with through hole apertures and the first and second sanitary fittings each having a first end and a second end with the second ends each having a flanged portion. The method includes inserting the first end of the first sanitary fitting into the aperture of the first member and positioning the flanged portion of the first sanitary fitting in the first member. The method also includes positioning the flanged portion of the second sanitary fitting in the first member. Further, the method includes engaging the second member over the first member such that a compressive force is applied to the first and second sanitary fittings.

Additionally, embodiments of a kit for assembling a pair of sanitary fittings each having a first end and a second end with the second ends each having a flanged portion is disclosed herein. The kit includes a first member having a through center aperture sized to receive the flanged portions and a plurality of resilient members such that, when compressed, sealingly connect the flanged portions. The kit also includes a second member having a generally concentric outer surface and a through center aperture.

Other embodiments of the invention are described in additional detail hereinafter.

BRIEF DESCRIPTION OF THE DRAWINGS

The description herein makes reference to the accompanying drawings wherein like reference numerals refer to like parts throughout the several views, and wherein:

FIG. 1A is a perspective view of an unassembled sanitary assembly containing a sanitary retainer according to a first embodiment of the present invention;

FIG. 1B is a perspective view of the sanitary assembly shown in FIG. 1A partially assembled;

FIG. 1C is a perspective view of the sanitary assembly shown in FIG. 1A fully assembled;

FIG. 2A is a sectional view of the unassembled sanitary assembly shown in FIG. 1A;

FIG. 2B is a sectional view of the sanitary assembly shown in FIG. 1A partially assembled;

FIG. 2C is a sectional view of the sanitary assembly shown in FIG. 1A fully assembled;

FIG. 13 is a sectional view of the sanitary retainer shown in FIG. 11;

FIG. 14 is a perspective view of a sanitary retainer according to a fourth embodiment of the present invention;

FIG. 15 is an elevation view of the sanitary retainer shown in FIG. 14;

FIG. 16 is a sectional view of the sanitary retainer shown in FIG. 14;

FIG. 17A is a perspective view of an unassembled sanitary assembly containing a sanitary retainer according to a fifth embodiment of the present invention;

FIG. 17B is a perspective view of the sanitary assembly shown in FIG. 17A partially assembled;

FIG. 17C is a perspective view of the sanitary assembly shown in FIG. 17A fully assembled;

FIG. 18A is an elevation view of the unassembled sanitary assembly shown in FIG. 1A;

FIG. 18B is an elevation view of the sanitary assembly shown in FIG. 17A partially assembled;

FIG. 18C is an elevation view of the sanitary assembly shown in FIG. 17A fully assembled;

FIG. 19 is an exploded perspective view of the sanitary retainer shown in FIG. 17A;

FIG. 20 is a side elevation view of the sanitary retainer shown in FIG. 17A;

FIG. 21 is another exploded perspective view of the sanitary retainer shown in FIG. 17A; and FIG. 22 is an elevation view of a collet of a sanitary retainer according to a sixth embodiment of the present invention.

DETAILED DESCRIPTION

Figures 3A, 3B, 3C:
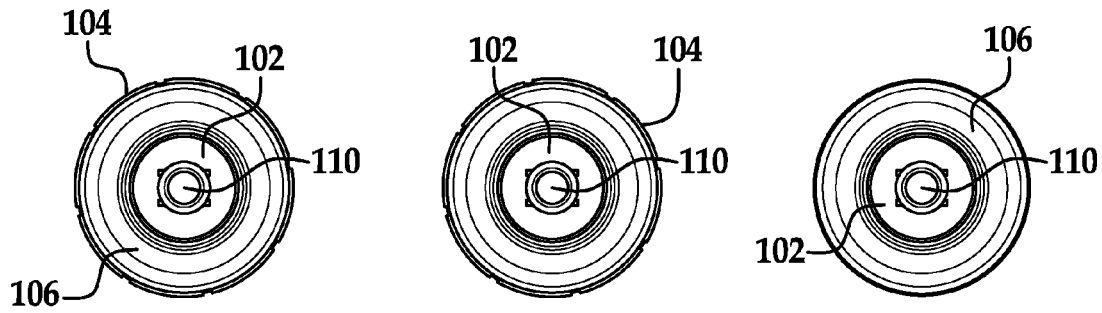
FIG. 3A is a top plan view of the unassembled sanitary assembly shown in FIG. 1A.
FIG. 3B is a top plan view of the sanitary assembly shown in FIG. 1A partially assembled.
FIG. 3C is a top plan view of the sanitary assembly shown in FIG. 1A fully assembled.
Figures 4A, 4B, 4C:
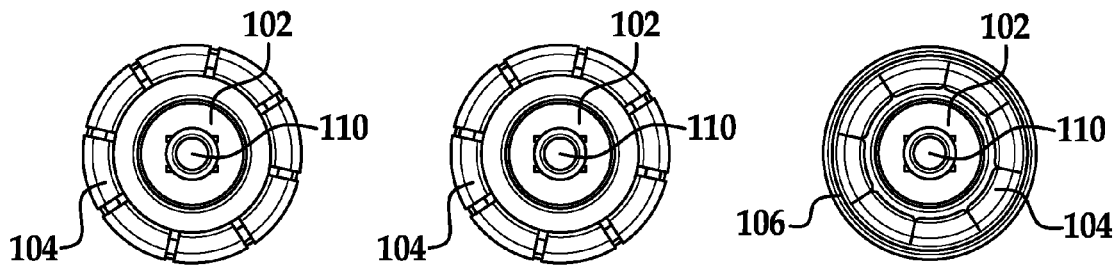
FIG. 4A is a bottom plan view of the unassembled sanitary assembly shown in FIG. 1A.
FIG. 4B is a bottom plan view of the sanitary assembly shown in FIG. 1A partially assembled.
FIG. 4C is a bottom plan view of the sanitary assembly shown in FIG. 1A fully assembled.

Referring to FIGS. 1A-1C, according to a first embodiment, a sanitary assembly 100 is shown in an unassembled configuration (FIG. 1A), a partially assembled configuration (FIG. 1B) and a fully assembled configuration (FIG. 1C). Generally, sanitary assembly 100 can include a pair of sanitary connectors 102, a sanitary retainer 103 and a gasket 105 (gasket shown in FIGS. 2A-2C). Sanitary retainer 103 can include a first member or collet 104 and a second member or sleeve 106. Both collet 104 and sleeve 106 can have a generally concentric outer surface.

Sanitary connectors 102 can include a tubular member 108 having a barb connection 110 at one end for connection to a tube (not shown) and an opposing end with a funnel formation 112 including an expanded circular opening with a flanged portion at a terminating end 114. Of course, other sanitary connectors are available that may have a different configuration (e.g. with no funnel formation). Sanitary connectors 102 can be made of any suitable material, such as a non-metal, which can permit the connectors to be heat welded to, for example, a propropylene or ethylene medical or pharmaceutical bag. The same or similar materials can be used in other applications in, for example, biotech, pharmaceutical, medical, foodstuff fitting connections and manifold applications. Sanitary connectors 102 can also be made from other plastics, stainless steel or any other suitable material as desired or required. Other configurations of sanitary connector 102 are also available. Gasket can be any suitable seal, such as an O-ring seal, and can be made of any suitable material. Collet 104 and sleeve 106 can be made from any suitable material such as propropylene and polyvinylidene difluoride.

Figures 5, 6:
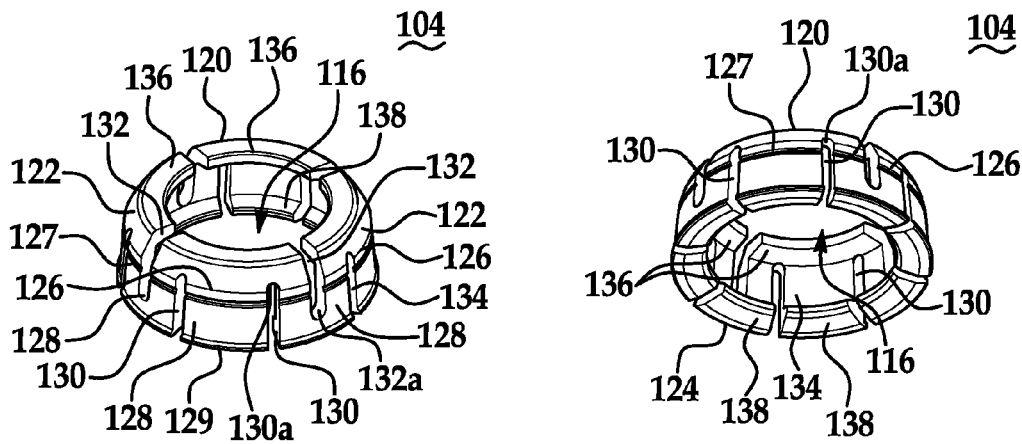
FIG. 5 is an exploded perspective view of a collet of the sanitary retainer shown in FIG. 1A.
FIG. 6 is another exploded perspective view of the collet shown in FIG. 1A.

Referring to FIGS. 5 and 6, collet 104 is an essentially annular member having a through aperture 116 for receiving gasket 105 and terminating ends 114 of the pair of sanitary connectors 102 therein. Collet 104 forms a discontinuous ring at a securing end 120 of an incurved portion 122. Incurved portion 122 begins at an annular edge 126. Proximate to the annular edge 126 and is an annular groove 127. Collet 104 also includes a receiving end 124 with resilient fingers 128 for radially contracting around terminating end 114. Fingers 128 are formed by narrow through slots 130 extending from receiving end 24 and terminating essentially at annular edge 126. Further slots 130 extend between lateral edges of adjacent fingers 128. Slots 130 are shown in the Figures with rounded termination ends 130a, however, the termination ends 130a may have pointed ends or any other suitably-shaped end.

Fingers 128 form a resilient seal by, as discussed in more detail below, forming a 360° compression around gasket 105 and terminating ends 114 of funnel formations 112. Each finger 128 contains a stop 129, where sleeve 106 contacts collet 504 when fully assembled. Between every other finger 28 there can be a through slot 132 which extends from securing end 120 to approximately a mid-section 134 of the associated finger 128. The through slots 132 can provide resiliency to the securing end 120 of collet 104 without sacrificing durability. Through slots 132 are shown in the Figures with rounded termination ends 132a, however, the termination ends 132a may have pointed ends or any other suitably-shaped end.

The interior surface 134 of collet 104 is essentially smooth except for a locking shelf 136 at securing end 120 and a resting shelf 138 at receiving end 124. Locking shelf 136 and resting shelf 138 can be designed and sized to permit through aperture 116 of collet 104 to have a diameter that is slightly smaller than terminating ends 114 for reasons that will be discussed in more detail hereinafter.

Figure 7:
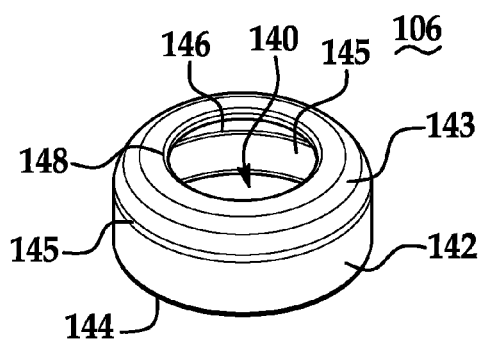
FIG. 7 is an exploded perspective view of a sleeve of the sanitary retainer shown in FIG. 1A.
Figure 8:
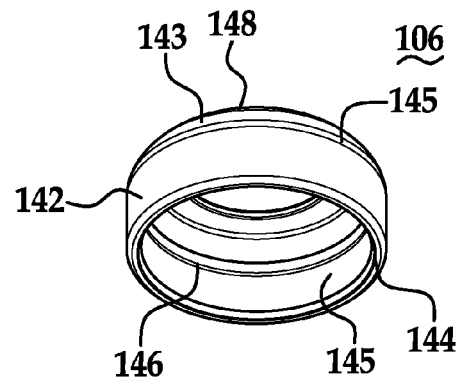
FIG. 8 is another exploded perspective view of the sleeve shown in FIG. 1A.

Referring to FIGS. 7 and 8, sleeve 106 is also an annular member with a through aperture 140 for receiving collet 104 therein. Sleeve 106 has a smooth exterior annular surface 142 and an incurved portion 143 beginning and extending inwardly from an annular edge 145. Sleeve 106 has a receiving end 144 forming an arcuate base to facilitate assembly to collet 104. An incurved portion begins at an annular edge 126. An interior surface 145 of sleeve 106 is essentially smooth throughout the length of sleeve 106 except for an annular projection 146 that extends from the interior surface 145. Annular projection 146 is sized and positioned on the sleeve 20 for disposition within annular groove 127 of collet 127 to form a lock when sanitary retainer 103 is engaged. Therefore, annular projection 146 can be positioned proximate to a securing end 148 of sleeve 106.

Referring to FIGS. 1A-1C, 2A-2C, 3A-3C and 4A-4C, during assembly, collet 104 is first placed over either one of the pair of sanitary connectors 102. Collet 104 and sleeve 106 can be loaded from the top or the bottom of the connection, allowing the operator to add the retainer before or after one of the barb connectors 110 of the sanitary connectors 102 is added to a tube (not shown). The terminating ends 114 of the sanitary connectors 102 can be placed into collet 104 to pre-hold sanitary connectors 102 and gasket 105 disposed between terminating ends 114 of sanitary connectors 102. As discussed previously, and as shown in FIGS. 1B and 2B, locking shelf 136 and resting shelf 138 on interior surface 134 of collet 104 hold sanitary connectors 102 and gasket 105 disposed therebetween so that sanitary connectors cannot easily move out of collet 104.

Sleeve 106 can then be slid over collet 104 by for example, the use of a tool (not shown). As sleeve 106 moves over collet 104, receiving end 144 of sleeve 106 initially encounters the securing end 144 of collet 104. Fingers 128 on collet 104 are pushed radially inwardly onto sanitary connectors 102 and gasket 105, so that a 360° compression provides a tight seal therebetween. Sleeve 106 continues over collet 18 until annular projection 146 on interior surface 145 of sleeve 106 sits within annular groove 127 of collet 106. To remove sanitary retainer 103, an operator may use a removal tool (not shown) so that disconnection and leakages are prevented.

Figure 9:
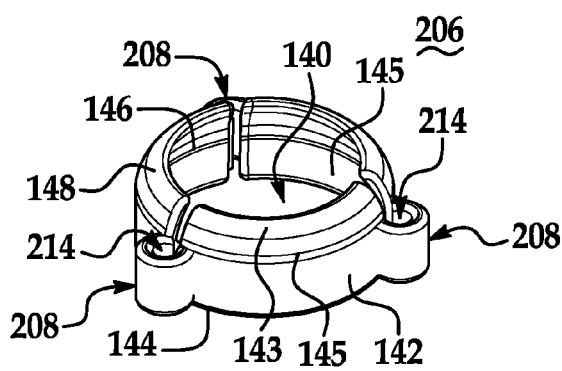
FIG. 9 is a perspective view of a sleeve of a sanitary retainer according to a second embodiment of the present invention.
Figure 10:
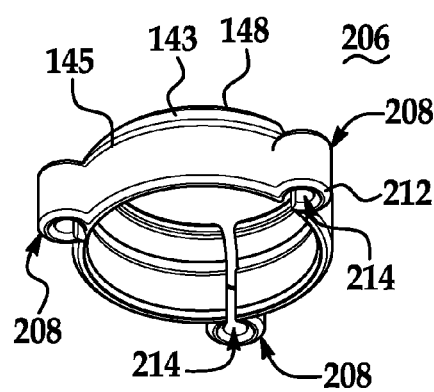
FIG. 10 is another perspective view of the sleeve shown in FIG. 9.

FIGS. 9 and 10 illustrate a sleeve 206 according to a second embodiment of the present invention. The second embodiment is similar to the first embodiment except that sleeve 206 has a number of springs 208. Each spring 208 projects outwardly from surface 142 to form an arch 212 having a through center aperture 214. Each spring 208 extends from receiving end 144 of sleeve 106 to annular edge 145. Springs 208 can accommodate the size variation of collets between, for example, different collet manufacturers. Springs 208 permit sleeve 206 to expand, when necessary, so that a collet having a diameter within a certain threshold can be received therein. Although three springs are shown in the Figures, sleeve 206 may also have more or less than three springs in alternative embodiments.

Figure 11:
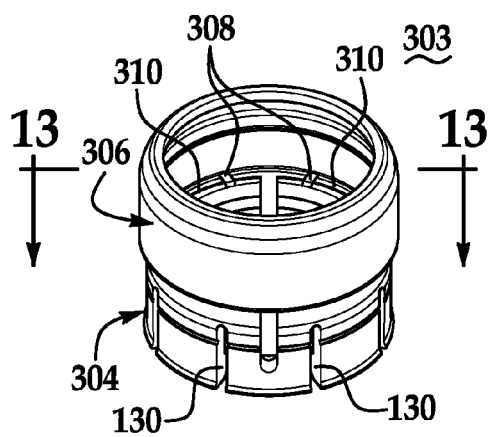
FIG. 11 is a perspective view of a sanitary retainer according to a third embodiment of the present invention.
Figure 12:
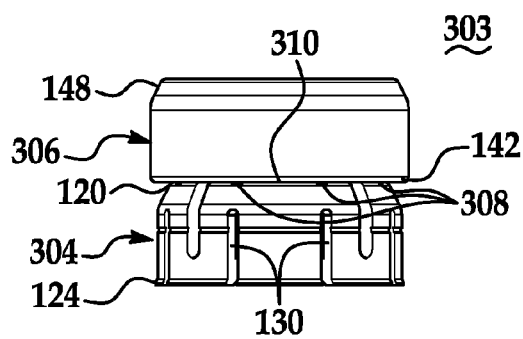
FIG. 12 is an elevation view of the sanitary retainer shown in FIG. 11.

FIGS. 11 and 12 illustrate a sanitary retainer 303 according to a third embodiment of the present invention. The third embodiment is similar to the first embodiment except that, the collet 304 and sleeve 306 are connected together by a plurality of frangible tabs 308. Frangible tabs 308 are connected to and extend horizontally from a radial surface of securing end 120 of collet 304. Opposing ends of frangible tabs 308 are also connected to an inner surface of sleeve 306. Frangible tabs can also extend vertically or in any other suitable direction to connect to sleeve 306. Frangible tabs 308 can be positioned, for example, in direct alignment with slots 130. Frangible tabs 308 can also be aligned in any other suitable manner. Although a plurality of frangible tabs 308 are shown, sanitary retainer 303 can contain one or more frangible tabs as required or desired.

The connection of frangible tabs 308 to the collet 304 and sleeve 306 form a gap 310 between the receiving end 142 of sleeve 306 and securing end 122 of collet 304 so that the frangible tabs 308 are the only connection therebetween when retainer 303 is in the unlocked position. The position of the frangible tabs 308 relative to collet 304 and sleeve 306 allow for breakage of frangible tabs 308 from collet 304 with a predetermined applied force.

During assembly, sanitary retainer 303 is first placed over either one of the pair of sanitary connectors 102. As discussed previously in connection with the first embodiment, terminating ends 114 of sanitary connectors 102 can be placed into collet 304 to pre-hold sanitary connectors 102 and gasket 105 disposed between terminating ends 114 of sanitary connectors 102. A locking instrument can be used to break the frangible tabs 308 to detach sleeve 308 from collet 302 and slide sleeve 306 over collet 304. Although frangible tabs 308 are broken away from collet 304, portions of frangible tabs 308 can remain intact on the inner surface of sleeve 306. Alternatively, all of the frangible tabs 308 can be broken away from both sleeve 306 and collet 304 or frangible tabs can remain intact on collet 304. When sleeve 306 is locked over collet 304, as discussed previously, the there is a 360° radial compression connection of sanitary connectors 102 and gasket 105.

Alternatively, in other embodiments, frangible tabs 308 can be replaced by a frangible meniscus of material (not shown). The frangible meniscus can be broken away from both the collet and the sleeve. The frangible meniscus can be connected to and extend from the radial surface of the securing end of the collet. The frangible meniscus can extend through the entire length of radial surface. Alternatively, frangible meniscus can extend to only a portion of the length of radial surface.

Opposing end portions of the frangible meniscus 428 can be positioned and connected to the wall of the interior expanded end portion 366 of the sleeve FIGS. 14-16 illustrate a sanitary retainer 406 according to a fourth embodiment of the present invention. The fourth embodiment is similar to the second embodiment except that, the collet 404 and sleeve 406 are connected together by a frangible connecting member such as a plurality of frangible tabs 408. Plurality of frangible tabs 408 are similar to plurality of frangible tabs 308 in the third embodiment.

Referring to FIGS. 17A-17C, and 18A-18C, according to a fifth embodiment, a sanitary assembly 500 is shown in an unassembled configuration (FIG. 17A), a partially assembled configuration (FIG. 17B) and a fully assembled configuration (FIG. 1C). Generally, as discussed in previous embodiments, sanitary assembly 500 can include a pair of sanitary connectors 102 and a sanitary retainer 503 and a gasket (not shown). Sanitary retainer 503 can include a collet 504 and a sleeve 506.

Referring to FIGS. 19-21, collet 504 is an essentially annular member having a through aperture 116 for receiving a gasket and terminating ends 114 of the pair of sanitary connectors 102 therein. Collet 504 forms a discontinuous ring at a securing end 120. Collet 504 also includes a receiving end 124 with resilient fingers 128 for radially contracting around terminating end 114. Fingers 128 are formed by narrow through slots 130 extending from receiving end 124 and terminating essentially at two thirds of the collet length. Slots 130 are shown in the Figures with rounded termination ends 130a, however, the termination ends 130a may have pointed ends or any other suitably-shaped end.

Fingers 128 form a resilient seal by, as discussed in more detail below, forming a 360° compression around gasket 105 and terminating ends 114 of funnel formations 112 when sleeve 506 is screwed onto collet 504. Each finger 128 contains a stop 129, where sleeve 506 contacts collet 504 when fully assembled. Between every other finger 28 there can be a through slot 132 which extends from securing end 120 to approximately a mid-section 134 of the associated finger 128. The through slots 132 can provide resiliency to the securing end 120 of collet 104 without sacrificing durability. Through slots 132 are shown in the Figures with rounded termination ends 132a, however, the termination ends 132a may have pointed ends or any other suitably-shaped end.

The inner surface of sleeve 506 contains a thread 510 and the outer or exterior surface of collet 504 contains a thread 512. Threads 510 and 512 can be, for example, an Acme thread. Threads 510 and 512 can also be any other suitable thread such as a square thread, a buttress thread, a tapered thread, or a tapered pipe thread.

Thread 510 can extend from securing end 148 of sleeve 506 to receiving end 144 of sleeve 506. Thread 512 can extend from securing end 120 of collet 504 to stop 129 of collet 504. During assembly, sanitary retainer 503 is first placed or positioned over either one of the pair of sanitary connectors 102. As discussed previously in connection with the first embodiment, terminating ends 114 of sanitary connectors 102 can be placed into collet 504 to pre-hold sanitary connectors 102 and the gasket disposed between terminating ends 114 of sanitary connectors 102. Sleeve 506 can then be screwed onto collet 504, creating a 360° radial compression connection of sanitary connectors 102 and gasket 105.

FIG. 22 illustrates a collet 604 according to a sixth embodiment of the present invention. The sixth embodiment is similar to the first embodiment except that collet 604 has a number of interlocks 608. Each interlock 208 includes a groove 610 for receiving a projection 612. Accordingly, each of resilient fingers 628 can include a groove 610 for receiving a projection 612 from an adjacent finger and a projection for interlocking with an adjacent finger. Each projection 612 is shown in the Figures as a trapezoidal shaped projection. However, projections may have pointed ends, square ends, rounded ends or any other suitably-shaped end. Grooves 610 will generally have the same shape as projections 612 so that as the sleeve (such as sleeve 106 of FIG. 1) moves over collet 604, interlocks 608 will hold collet 604 together. As such collet 604 will move into the sleeve when the sleeve does not contact the bottom of the collet. Accordingly, an operator does not have to turn and close the retainer containing collet 604 after the sleeve has been secured on the collet (as discussed in connection with FIG. 1)

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed:

1. A kit for assembling a pair of sanitary fittings each having a first end and a second end, the second ends each having a flanged portion, the kit comprising:
    a first member having an annular sidewall, a first end defining a first discontinuous ring, an opposing second end defining a second discontinuous ring, and a through center aperture defined by the annular sidewall sized to receive the flanged portions of the sanitary fittings; and
    a second member having an annular sidewall that is generally concentric with the annular sidewall of the first member and a through center aperture defined by the annular sidewall of the second member,
    wherein the first end of the first member has a flange extending radially inwardly and defining a circumferential channel adapted to engage the flanged portions of the sanitary fittings, and the second member is adapted to surround at least a majority of the first member, reduce an unassembled diameter of each of the first and second discontinuous rings, and form a 360° compression around the flange portions,
    wherein the first member has an outer threaded surface, the second member has an inner threaded surface adapted to mate with the outer threaded surface of the first member when assembled, and at least one of the plurality of first axial grooves extends into the outer threaded surface of the first member.

2. The kit of claim 1, wherein the first and second member each comprise a non-metal material.

3. The kit of claim 2, wherein the first and second members each comprise a propylene, a polyvinylidene difluoride, or a combination thereof.

4. The kit of claim 1, wherein the inner threaded surface of the second member extends from the first end of the second member to the second end of the second member, and wherein the first member includes a stop near the second end of the first member adapted to contact the second end of the second member when the first and second members are in an assembled configuration, and the outer threaded surface of the first member extends from the first end of the first member to the stop of the first member.

5. The kit of claim 1, wherein the first member defining a plurality of second axial grooves each terminating at the second end.

6. The kit of claim 5, wherein at least one of the plurality of first axial grooves extends between a pair of the plurality of second axial grooves.

7. The kit of claim 1, wherein at least one of the plurality of first axial grooves extends into the outer threaded surface of the first member.

8. The kit of claim 1, wherein the threaded surface includes a square thread, a buttress thread, a tapered thread, or a tapered pipe thread.

* * * * *